United States Patent
Hinson, Jr.

(10) Patent No.: US 9,611,086 B2
(45) Date of Patent: Apr. 4, 2017

(54) REUSABLE SURGICAL WRAPPERS

(71) Applicant: Hinson & Hale Medical Technologies, Inc., Wilkesboro, NC (US)

(72) Inventor: Rea Hinson, Jr., Pittsboro, NC (US)

(*) Notice: Subject to any disclaimer, the term of this patent is extended or adjusted under 35 U.S.C. 154(b) by 349 days.

(21) Appl. No.: 13/674,905

(22) Filed: Nov. 12, 2012

(65) Prior Publication Data

US 2013/0168278 A1    Jul. 4, 2013

Related U.S. Application Data

(60) Provisional application No. 61/558,876, filed on Nov. 11, 2011.

(51) Int. Cl.
- B65D 85/00 (2006.01)
- A61B 50/31 (2016.01)
- A61B 50/30 (2016.01)

(52) U.S. Cl.
CPC .............. *B65D 85/00* (2013.01); *A61B 50/30* (2016.02); *A61B 50/31* (2016.02); *A61B 2050/314* (2016.02); *A61B 2050/316* (2016.02)

(58) Field of Classification Search
CPC ........ B65D 29/00; B65D 31/04; B65D 33/00; B65D 75/26; B65D 88/1612; B65D 31/02; B65D 31/08; B65D 81/264; B65D 29/04; B65D 85/00; A61B 50/30; A61B 50/31; A61B 2050/314; A61B 2050/316
USPC .......................... 206/438; 383/107, 113, 117
See application file for complete search history.

(56) References Cited

U.S. PATENT DOCUMENTS

| | | | | |
|---|---|---|---|---|
| 5,073,488 A | * | 12/1991 | Matner et al. | 435/31 |
| 5,199,795 A | * | 4/1993 | Russo et al. | 383/113 |
| 5,222,600 A | * | 6/1993 | Stoddard et al. | 206/370 |
| 5,244,718 A | * | 9/1993 | Taylor et al. | 442/208 |
| 5,431,970 A | * | 7/1995 | Broun et al. | 428/36.5 |
| 5,715,943 A | * | 2/1998 | Thompson, Jr. | 206/363 |
| 6,613,035 B1 | * | 9/2003 | Longo et al. | 604/403 |
| 7,718,433 B2 | * | 5/2010 | Stecklein | A61L 2/07 422/119 |
| 2003/0123759 A1 | * | 7/2003 | Banks | 383/88 |
| 2003/0170453 A1 | * | 9/2003 | Foss | A01N 57/16 428/373 |
| 2005/0255776 A1 | * | 11/2005 | Howland | B32B 5/26 442/286 |
| 2006/0134414 A1 | * | 6/2006 | Neuberg | D01F 1/10 428/372 |

* cited by examiner

*Primary Examiner* — Peter Helvey
(74) *Attorney, Agent, or Firm* — J. Bennett Mullinax, LLC

(57) ABSTRACT

Surgical wrappers and related methods are provided. A reusable surgical wrapper can include a first layer that includes a fabric having at least one of synthetic fibers or synthetic yarns. In some embodiments, a surgical wrapper can include a first layer comprising a first fabric that repels fluids forming a first face of the surgical wrapper. A second layer can be provided that includes a second fabric forming a second face of the surgical wrapper. A seam binding can be disposed around at least a portion of an outer edge of the first fabric and an outer edge of the second fabric to join the first layer and the second layer to form a dual layered surgical wrapper.

8 Claims, 7 Drawing Sheets

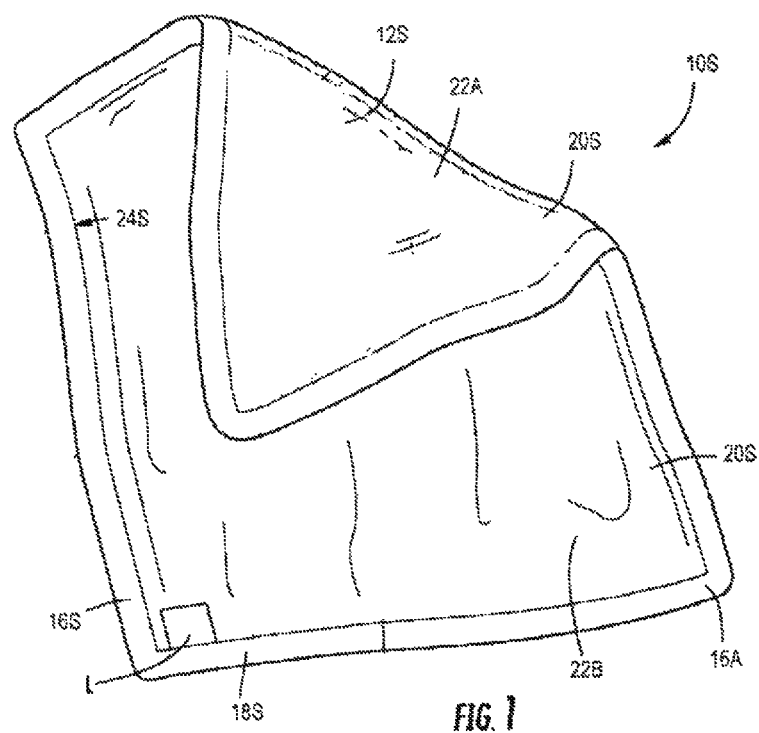

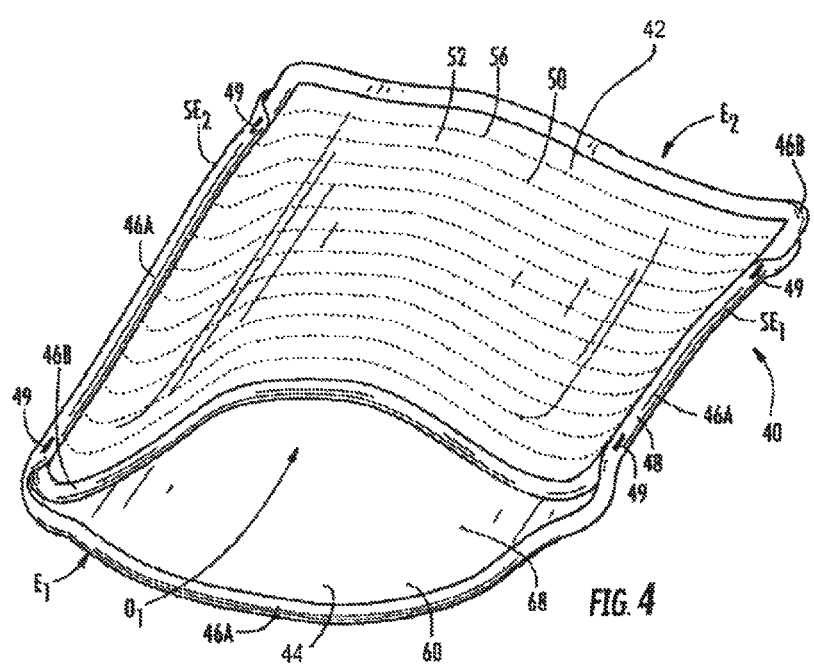

REUSABLE SURGICAL WRAPPERS

RELATED APPLICATIONS

This application claims priority to U.S. Provisional Patent Application Ser. No. 61/558,876, filed Nov. 11, 2011, the entire contents of which is hereby incorporated by reference herein.

TECHNICAL FIELD

The subject matter disclosed herein relates generally to wrappers used to cover a medical device to keep the medical device sterile. More specifically, the subject matter disclosed herein relates to surgical wrappers used to enclose surgical instruments, devices and equipment to facilitate sterilization and to maintain sterility until use.

BACKGROUND

Surgeries require much preparation and standardization of procedures. One of the areas where preparation is especially helpful is in assembly and organization of surgical instruments, surgical textiles, and devices that are to be used during a surgery or within a surgical environment. A major concern is the sterilization and the maintenance of sterilization of those surgical instruments and devices. Sterilization is a process which achieves the complete destruction or killing of all microorganisms, including bacterial spores.

Sterilization can be accomplished by, for example, the use of steam under pressure (autoclaving), the use of dry heat (hot air oven), and/or the use of chemicals such as ethylene oxide gas (which is mainly used in industry) or other low temperature methods (e.g., hydrogen peroxide gas plasma). Sterilization through the use of steam under pressure can have several advantages in providing sterilized surgical instruments and devices. Such sterilization using an autoclave can be highly effective and can provide rapid heating and rapid penetration of instruments. Such sterilization can also be nontoxic and inexpensive.

Steps of sterilization through the use of steam under pressure, for example, in an autoclave, can include cleaning all surgical instruments and devices to be sterilized. To begin, the surgical instruments, surgical textiles, and devices can be opened or unlocked at the hinges of hinged items and/or disassembled for items with multiple pads. All labeled packs, drums, or unwrapped items in the chamber of the autoclave can be arranged in a way that allows the steam to circulate freely. Once the steam has circulated under the correct temperature and pressure for the correct amount of time, the steam can be released and the items left to dry completely. Items such as packs, drums or unwrapped items should be handled with sterile instruments after they have cool to room temperature.

For unwrapped items, use needs to be immediately after removal from the autoclave. Alternatively, such items need to be kept in a covered, dry, sterile container that can be stored for later use. To better preserve the sterilization, surgical instruments and devices can be wrapped beforehand and then sterilized. Wrapping instruments and other items before steam sterilization helps to decrease the likelihood that, after sterilization, they will be contaminated before use.

For wrapped items, the length of time of storage (i.e., shelf life) that a wrapped, sterile item is considered sterile depends on whether or not a contaminating event occurs not necessarily on how long an item has been stored. Items should be stored in a closed, dry, cabinet with moderate temperature and low humidity in an area that is not heavily trafficked. A wrapped pack can be considered sterile as long as it remains intact and dry.

The materials used to wrap instruments can vary widely in their type and effectiveness. Most of these wrappers are single use disposable and their shelf life can vary greatly. Further, for both disposable and non-disposable wrappers, the wrappers are often dyed to specific colors. For instance, wrappers can be dyed to match the color the surgical scrubs and/or other linens used in an operating room. For example, the wrappers can be dyed to match the color of the surgical scrubs and linens (hues of blue, green and pink). In such colored surgical wrappers, the dye used to color the wrappers in some instances can be released and transferred from the fabrics used in the wrappers when the wrappers are exposed to the intense pressures, moisture and temperatures during steam sterilization. Thus, dye, color, or colorant material transfer occurs, which is undesirable, but the dye or color that is transferred can pool on the instruments, textiles and containers within the sterilized wrappers. While the instruments are still sterile and completely safe for use, the undesirable color on the instruments can be disconcerting to surgeons and operating room staff. A need exists for a reusable surgical wrapper that can facilitate steam sterilization, provide appropriate shelf life for sterilized items and not be subject to color transfer.

SUMMARY

It is an object of the present disclosure to provide novel surgical wrappers used to enclose surgical instruments, textiles, devices and equipment to facilitate sterilization and to maintain sterility until use. The surgical wrappers disclosed herein can be used to enclose another medical device that is to be sterilized by a health care provider. The surgical wrappers disclosed herein can allow sterilization of the enclosed medical device and can aid in the maintaining of sterility of the enclosed device until use and can be reused after later reprocessing to launder, inspect, and sterilize the surgical wrapper again.

A few objects of the presently disclosed subject matter having been stated hereinabove, and which are achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIG. 1 illustrates a perspective view of an embodiment of a reusable surgical wrapper according to the subject matter disclosed herein;

FIG. 4 illustrates a perspective view of the embodiment of the reusable surgical wrapper according FIG. 3 from an opposite end and opposite exterior face of the reusable surgical wrapper;

DETAILED DESCRIPTION

Figure 2A:
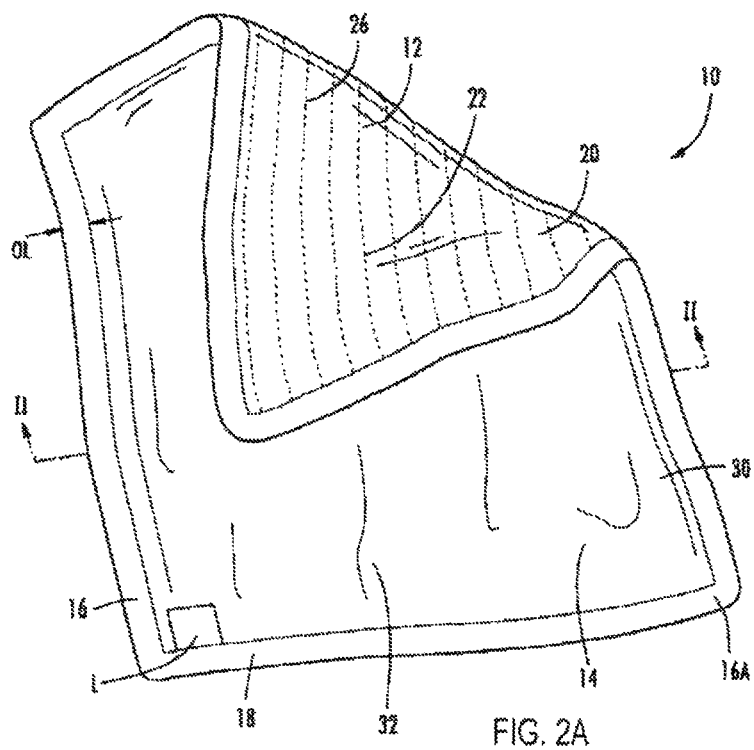
FIG. 2A illustrates a perspective view of an embodiment of a reusable surgical wrapper according to the subject matter disclosed herein.

Reference will now be made in detail to the description of the present subject matter, one or more examples of which are shown in the figures. Each example is provided to explain the subject matter and not as a limitation. In fact, features illustrated or described as part of one embodiment may be used in another embodiment to yield still a further embodiment. It is intended that the present subject matter cover such modifications and variations.

The surgical wrappers disclosed herein are medical devices intended to be used to enclose another medical device that is to be sterilized by a health care provider. The surgical wrappers of the subject matter disclosed herein can allow sterilization of medical devices and instruments wrapped and enclosed therein and can also maintain sterility of the enclosed device until use. The surgical wrappers can be provided nonsterile and can be processed before use.

The surgical wrappers disclosed herein can be subject to approved laundering and sterilization processes and can be reused a number of times. For example, the surgical wrappers disclosed herein can be reprocessed for between about 2 and about 150 uses. For instance, the surgical wrappers disclosed herein can be reprocessed for about 100 uses when laundered and sterilized according to approved methods for surgical reuse. For example, the surgical wrappers disclosed herein can be reprocessed based on industrial laundering procedures and steam sterilization that include placing the items in prevacuum setting at a 270° F. temperature for 4 minutes with 20 minutes drying time.

In some embodiments, the surgical wrappers according to the present disclosure can comprise a single layer fabric that can be a woven or knitted fabric. The single layer fabric can comprise yarns comprising synthetic fibers or blends of synthetic and natural fibers. The yarns of synthetic fibers or blends of synthetic and natural fibers can be treated and processed so that the synthetic fibers can be a fluid absorbent or repellent. The synthetic yarns or fibers used in the fabric can be solution dyed fibers or yarns to prevent transfer of color, or colorant, from the synthetic fibers or yarns to the instruments or containers within the wrapper during the steam sterilization process. In particular, colorant material, or dyestuffs, such as pigments used to obtain a desired color can be mixed in with the molten polymer of the synthetic material used to form the synthetic fibers or yarns. For example, during fiber formation for synthetic fibers used in staple fiber yarns, such as blended yarns that comprise synthetic fibers and natural fibers or other synthetic yarn, the color pigments are added before the polymeric synthetic material is extruded into continuous fibers that can then be processed into appropriate staple lengths. Similarly, for filament yarns, the color pigments are added before the polymeric synthetic material is extruded info continuous fibers that form the continuous filament yarns. This process allows the color to become an inherent part of the synthetic yarns or the synthetic fibers in the yarns. Such solution dyed synthetic fibers or yarns that can be used to form the fabric used in the reusable wrappers can include, for example, nylon, polyester, and acrylic.

In some embodiments, the surgical wrappers according to the present disclosure can comprise a single layer knitted fabric. The single layer knitted fabric can be a polyester fabric that has been treated and processed to form a fluid absorbent fabric. For example, the polyester absorbent fabric can be an INFUSED® fabric sold by Hinson & Hale Medical Technologies, Inc. of Wilkesboro, N.C. The single layer knitted fabric can have a seam binding that extends around an outer edge of the fabric. For example, the seam binding can extend around the entire outer edge of the fabric.

In some embodiments, the surgical wrappers according to the present disclosure can also comprise dual layers that facilitate the sterilization of surgical items that are stored therein and also facilitate the maintenance of the sterility of those surgical items. The fabric or fabrics of the dual layered surgical wrappers can comprise yarns comprising synthetic fibers or blends of synthetic and natural fibers. The yarns of synthetic fibers or blends of synthetic and natural fibers can be treated and processed so that the synthetic fibers can be a fluid absorbent. The synthetic yarns or fibers used in the fabric can be solution dyed fibers or yarns to prevent transfer of color, or dye stuff, such as pigments, from the synthetic fibers or yarns during the steam sterilization process.

In some embodiments, the surgical wrapper can be a knit fabric with a first face of the knit fabric comprising the first layer and a second face of the knit fabric comprising the second layer. In some embodiments, the surgical wrapper can be two fabrics bound together. For example, the first layer of the surgical wrapper can be a first fabric and the second layer can be a second fabric with the first and second fabrics being bound together.

In some embodiments, both layers can be formed from fabric or fabrics that comprise solution dyed fibers or yarns. For example, one or both layers can include fabric that comprises synthetic fibers or yarns, such as polyester, acrylic, nylon, or the like, that have been solution dyed. Further, in some embodiments, both layers of the surgical wrapper can be barrier layers that can repel fluids. In some embodiments, one layer can be a barrier layer that can repel fluids and the other layer can be an absorbent layer that can soak up such fluids when the absorbent layer comes in contact with these fields.

For example, a surgical wrapper can comprise a first layer comprising a first fabric that repels fluids forming a first exterior face of the surgical wrapper and a second layer comprising a second fabric forming a second exterior face of the surgical wrapper. The surgical wrapper can also comprise a seam binding disposed around at least a portion of an outer edge of the first fabric and at least a portion of an outer edge of the second fabric to join the first layer and the second layer. In some embodiments, both the first and second fabrics can be barrier fabrics that can repel bodily and other fluids. In some embodiments, the first fabric can be a barrier fabric that can repel bodily and other fluids and the second fabric can be an absorbent fabric that can soak up such fluids when the absorbent fabric comes in contact with these fluids.

The first fabric can comprise woven synthetic yarns, blended yarns of one or more synthetic fibers, or blended yarns of synthetic and natural fibers. The first fabric can be tightly woven. The synthetic material used in the fibers and/or yarns can comprise polyester, acrylic, nylon, or the like. For example, in some embodiments, the first fabric of the first layer can comprise woven polyester yarns that can be tightly woven. In some embodiments, the first fabric can also include a plurality of static dissipative yarns. For example, the plurality of static dissipative yarns can comprise carbon filament yarns. In some embodiments, the plurality of static dissipative yarns can comprise between about 0% and about 2% of the first fabric.

The second fabric can comprise woven synthetic yarns, blended yarns of one or more synthetic fibers, or blended yarns of synthetic and natural fibers. The synthetic material used in the fibers and/or yarns can comprise polyester, acrylic, nylon, or the like. For example, in some embodiments, the second fabric can comprise a woven polyester fabric that is treated and processed with a fluid repellent finish in a similar manner to the first fabric that is a barrier fabric. Alternatively, the second fabric can comprise a woven polyester fabric is treated and processed to form an absorbent fabric. For example, the polyester absorbent fabric can be an INFUSED® fabric sold by Hinson & Hale Medical Technologies, Inc., of Wilkesboro, N.C. With such a treatment, the second fabric can be highly absorbent.

In some embodiments, the first layer and the second layer can form an opening therebetween to expose an interior face of the first fabric and an interior face of the second fabric. For example, in some embodiments, the first layer and the second layer can form an opening at two opposing ends of the dual layered surgical wrapper with the openings forming an aperture through the dual layered surgical wrapper. In some embodiments, the seam binding can comprise one or more fabric strippings that are disposed around at least a portion of the outer edge of the first fabric and one or more fabric strippings that are disposed around at least a portion of the outer edge of the second fabric. The one or more fabric strippings disposed around at least a portion of the outer edge of the first fabric and one or more fabric strippings disposed around at least a portion of the outer edge of the second fabric can at least partially overlap on opposing sides of the dual layered surgical wrapper. In such a manner, the first layer and the second layer can form an opening therebetween to expose an interior face of the first fabric and an interior face of the second fabric. In particular, the first layer and the second layer can form an opening at two opposing ends of the dual layered surgical wrapper with the openings forming an aperture through the dual layered surgical wrapper.

In some embodiments, the seam binding can comprise one or more fabric strippings that am disposed around the entire outer edge of the first fabric and the entire outer edge of the second fabric to form a closed dual layered surgical wrapper.

Referring to FIG. 1, an embodiment of a reusable surgical wrapper, generally designated IDS, can be provided according to the present disclosure. Surgical wrapper 10S can comprise a single layer 12S that can comprise a fabric 20S. Fabric 20S can comprise synthetic yarns or yarns comprising synthetic fibers or blends of synthetic and natural fibers. Fabric 20S can repel and/or absorb fluids. Fabric 20S can comprise a first face 22A and a second face 22B. Layer 12S can have a seam binding 16S around an outer perimeter 18S of surgical wrapper 10S to provide finished sides layer 12. For example, the seam binding can be a clean finish bias binding 16S. In some embodiments, clean finish bias binding 16S can comprise hemmed edges 24S of fabric 20S around perimeter 18S. In some embodiments, clean finish bias binding 16S can be made of different material. For example, clean finish bias binding 16S can foe strips of a fabric, such as a fabric stripping 16A that are sown around outer edges of fabric 20S. For instance, fabric stripping 16A can comprise a fabric comprising synthetic yarns, blended yarns of synthetic fibers, or blended synthetic and natural fibers. In some embodiments, fabric stripping 16A can be a tightly woven synthetic fabric comprising yarns and/or fibers of polyester, acrylic, nylon or the like.

Surgical wrapper 10S can also comprise a label L with identifying information and a grid or radio frequency identification (RFID) chip to indicate the number of reprocessing cycles performed to ensure that surgical wrapper 10S is not used past a set number of cycles, for example, 100. Surgical wrapper 10S can comprise different sizes for different uses. For example, surgical wrapper 10S can comprise sizes such as about 18 inches×about 18 inches, about 24 inches×about 24 inches, about 30 inches×about 30 inches, about 36 inches×about 36 inches, about 45 inches×about 45 inches, about 54 inches×about 54 inches, and about 72 inches×about 72 inches. Further, surgical wrapper 10S can be made to specified dimensions based on the application in which it is to be used in or cut of an operating room.

Fabric 20S and, if applicable fabric strippings 16A, can comprise yarns comprising synthetic fibers or blends of synthetic and natural fibers. The yarns of synthetic fibers or blends of synthetic and natural fibers can be treated and processed so that the synthetic fibers can be a fluid absorbent or fluid repellent. The synthetic yarns or fibers used in the fabric 20S can be solution dyed fibers or yarns to prevent transfer of color from the synthetic fibers or yarns during the sterilization process. In particular, dye material, such as water insoluble pigments used to obtain a desired color can be mixed in with the molten polymer of the synthetic material used to form the synthetic fibers or yarns. For example, during fiber formation for synthetic fibers used in staple fiber yarns, such as blended yarns that comprise synthetic fibers and natural fibers or other synthetic yarn, pigment color is added before the polymeric synthetic material is extruded into continuous fibers that can then be processed into appropriate staple lengths. Similarly, for filament yarns, the pigment color is added before the polymeric synthetic material is extruded into continuous fibers that form the continuous filament yarns. This process allows the color to become an inherent pad of the synthetic yarns or the synthetic fibers in the yarns. Such solution dyed synthetic fibers or yarns that can be used to form the fabric used in the reusable wrappers can include, for example, nylon, polyester, and acrylic.

Using solution dyed fibers and/or yarns can allow wrapper 10S to have specific colors. For instance, wrapper 10S can be colored to match the color the surgical scrubs and/or other linens used in an operating room. In some embodiments, wrapper 10S can be colored to match the color of the surgical scrubs and linens (hues of blue, green and pink). The fibers and/or yarns can be colored by adding insoluble pigments into the polymer from which the synthetic fibers are made before the extrusion process used to form the polymer into the fibers and/or yarns. In such colored surgical wrapper 10S, the pigments used to color wrapper 10S will not release, transfer, or leach from the synthetic yarns or fibers used in wrapper 10S when wrapper 10S is exposed to the intense pressures and temperatures during steam sterilization since the pigment is insoluble in water and is embedded in the synthetic fibers and/or yarns formed during the solution dye process. Fading and the coloring of instruments contained in wrapper 10S during use, as explained below, can thus be prevented.

Such a single layered wrapper 10S can also be used as a surgical towel. For example, wrapper 10S can comprise a single layer knitted fabric. The single layer knitted fabric can be a polyester fabric that has been treated and processed to form a fluid absorbent fabric.

When fabric 20S is made to be repellent, chemicals, such as repellent finishes, that can be used in the finishing process to increase repellency. When fabric 20S is made to be absorbent, fabric 20S and the synthetic yarns therein can be treated with chemicals in a finishing process to make the synthetic containing fabric, which is naturally hydrophobic when untreated, absorbent and hydrophilic. For example, the fabric 20S can comprise polyester fibers and/or polyester yarns therein that can be treated with chemicals in a finishing process to make the polyester containing fabric, which is naturally hydrophobic when untreated, absorbent and hydrophilic. For example, the polyester fabric of second fabric 20S can be INFUSED® fabrics sold by Hinson & Hale Medical Technologies, Inc. located in Wilkesboro, N.C. Such fabrics are considered fluid absorbent fabrics, in particular, second fabric 20S can be highly absorbent.

Figure 2B:
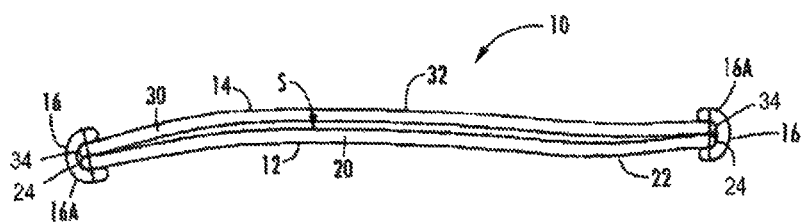
FIG. 2B illustrates a cross-sectional schematic view of the embodiment of the surgical wrapper according to FIG. 2A taken along the lines II-II.

Referring to FIGS. 2A and 2B, an embodiment of a reusable surgical wrapper, generally designated 10, can be provided according to the present disclosure. Surgical wrapper 10 can comprise a first layer 12 and a second layer 14. First layer 12 and second layer 14 of surgical wrapper 10 can have a seam binding 16 around an outer perimeter 18 of surgical wrapper 10 to bind first layer 12 and second layer 14 together to form surgical wrapper 10. For example, in some embodiments, seam binding 16 can be a clean finish bias binding. First layer 12 can comprise a first fabric 20 that can repel fluids. First fabric 20 can form a first exterior face 22 of surgical wrapper 10. Second layer 14 can comprise a second fabric 30 that absorbs fluids forming a second exterior face 32 of surgical wrapper 10. Surgical wrapper 10 can also comprise a label L with identifying information and a grid or RFID chip to indicate the number of reprocessing cycles performed to ensure that surgical wrapper 10 is not used past a set number of cycles, for example, 100. Surgical wrapper 10 can comprise different sizes for different uses. For example, surgical wrapper 10 can comprise sizes such as about 18 inches×about 18 inches, about 24 inches×about 24 inches, about 30 inches×about 30 inches, about 36 inches×about 36 inches×about 45 inches×about 45 inches, about 54 inches ×about 54 inches, and about 72 inches×about 72 inches. Further, surgical wrapper 10 can be made to specified dimensions based on the application in which it is to be used of the desired dimensions of the customer.

First and second fabrics 20, 30 can comprise woven or knitted fabrics. In some embodiments, first and second fabrics 20, 30 can comprise synthetic yarns or yarns comprising synthetic fibers or blends of synthetic and natural fibers. Further, in some embodiments, first and second fabrics 20, 30 can comprise solution dyed fibers or yarns as explained above.

In some embodiments, first fabric 20 can comprise a barrier fabric that composes spun yarns comprising synthetic fibers, filament yarn comprising synthetic fibers or a combination thereof. In some embodiments, first fabric 20 can comprise a woven or a knitted fabric. For example, in soma embodiments, first fabric 20 of first layer 12 can comprise woven fabric. For instance, first fabric 20 can comprise a polyester fabric that comprises polyester yarns that can be tightly woven. The polyester fabric of first fabric 20 can be finished to make it fluid repellent, thereby by forming a harrier fabric. Commercially available chemicals, such as repellent finishes, that can be used in the finishing process to increase repellency. First fabric 20 can vary in weight and size. For example, in some embodiments, first fabric 20 can, for example, have a weight per unit area between about 2 oz/yd$^2$ and about 4 oz/yd$^2$.

In some embodiments, first fabric 20 can comprise a plurality of static dissipative yarns 26. For example, the plurality of static dissipative yarns 26 can comprise carbon filament yarns. In some embodiments, the plurality of static dissipative yarns 26 can comprises between about 0% and about 2% of the first fabric 20. For example, static dissipative yarns 26 can be added every certain number of ends or picks. In some embodiments, static dissipative yarns 26 can be larger yarns in weight and weight per unit length that the polyester yarns that comprise the rest of first fabric 20. In some embodiments, static dissipative yarns 26 can be smaller yarns in weight and weight par unit length that the polyester yarns that comprise the rest of first fabric 20.

In some embodiments, second fabric 30 can comprise a fabric that comprises spun yarns comprising synthetic fibers, filament yarn comprising synthetic fibers or a combination thereof. In some embodiments, second fabric 30 can comprise a woven or a knitted fabric in some embodiments, second fabric 30 can comprise a barrier fabric or an absorbent fabric.

In some embodiments, second fabric 30 can be a barrier fabric that can comprise woven yarns, for example, polyester yarns, that are treated with a fluid repellent finish in a similar manner to first fabric 20 that can serve as a barrier fabric. In some embodiments, second fabric 30 can comprise an absorbent fabric that can absorb fluids. For example, the absorbent polyester fabric can comprise woven polyester yarns, such as spun polyester yarns. The absorbent polyester fabric can be treated to create absorbency. Alternatively, the polyester yarns of the absorbent polyester fabric can be filament yarns with the fabric and yarns treated to create absorbency. Second fabric 30 can comprise a lightly woven polyester fabric. Second fabric 30 can alternatively be a knitted fabric. For example, second fabric 30 can be a polyester knitted fabric with the same performance characteristics as the woven polyester fabric. Second fabric 30 can vary in weight and size. For example, in some embodiments, second fabric 30 can be a spun polyester woven fabric that has a weight per unit area that can range between about 4 oz/yd$^2$ and about 5 oz/yd$^2$.

The polyester fabric of second fabric 30 and the polyester yarns therein can be treated with chemicals in a finishing process to make the polyester fabric, which is naturally hydrophobic when untreated, absorbent and hydrophilic. For example, the polyester fabric of second fabric 30 can be INFUSED® fabrics sold by Hinson & Hale Medical Technologies, Inc. located in Wilkesboro, N.C. Such fabrics are considered fluid absorbent fabrics, in particular, second fabric 30 can be highly absorbent.

Clean finish bias binding 16 can be disposed around an outer edge 24 of first fabric 20 and an outer edge 34 of second fabric 30 to join first layer 12 and second layer 14. In particular, as shown in FIG. 2A, seam binding 16 can extend around all outer edges 24, 34 of both first fabric 20 and second fabric 30 to form a closed dual layered surgical wrapper 10 wherein access to the area between the layers is prohibited unless a portion of surgical wrapper 10 is torn or seam binding 16 removed. As can be seen in FIG. 2B which is a schematic cross-sectional view taken along the lines II-II, first fabric 20 and second fabric 30 can. In some embodiments, be secured together by only seam binding 16 on the perimeter of surgical wrapper 10. Thus, first layer 12 and second layer 14 of the dual layered surgical wrapper 10 can be secured only at the perimeter of surgical wrapper 10. In this manner, the body of first fabric 20 inside of outer edge 24 can move separately from the body portion of second fabric 30 inside of outer edge 34. Since first fabric 20 and second fabric 30 are not secured to each other in the body portions and can move separately horn one another, a space S can be created between an inferior face 26 of first fabric 20 and an interior face 36 of second fabric 30.

Clean finish bias binding 16 can be made of different material. For example, clean finish bias binding 16 can be strips of a fabric, such as a fabric stripping 16A. For instance, fabric stripping 16A can be a tightly woven polyester fabric. Fabric stripping 16A can have different widths and lengths. The width can depend on the amount of overlap OL of fabric stripping 16A on exterior face 22 of first fabric 20 and exterior face 32 of second fabric 30. For example, fabric stripping 16A can range in width from about 0.25 inches to about 1 inch. Overlap OL can vary, for example, between about 0.1 inches to about 0.5 of inches. While not shown in the schematic view FIG. 2B to increase the clarity of the information being conveyed therein, in some embodiments, fabric stripping 16A can be about 1.5 inches in width and can be folded to a clean finish of about 0.5 inch on the exterior faces 22, 32, of first fabric 20 and second fabric 30, respectively. The length can depend on the size of surgical wrapper 10 and the length of its outer perimeter 18. The length can also depend on the number of fabric strippings 16A that are used in surgical wrapper 10. For example, in the embodiment depicted in FIG. 1, a single fabric stripping 16A can be used to create clean finish bias binding 16. In some embodiments, fabric stripping 16A can comprise a fluid repellent fabric. Alternatively, in some embodiments, fabric stripping 16A can comprise an absorbent fabric, in this manner, clean finish bias binding 16 can seal outer edges 24, 34 of first fabric 20 and second fabric 30.

Clean finish bias binding 16 can be secured around outer edge 24 of first fabric 20 and outer edge 34 of second fabric 30 in different manners. For example, clean finish bias binding 16 can be adhered to outer edges 24, 34 by a permanent adhesive. Alternatively, clean finish bias binding 16 can be secured around outer edge 24 of first fabric 20 and outer edge 34 of second fabric 30 by a stitching, in some embodiments, the stitching can be a strong thread such as multiplied polyester multifilament thread, in some embodiments, the stitching can be made from a spun polyester thread. The stitching can be tight to seal outer edge 24 of first fabric 20 and outer edge 34 of second fabric 30 together.

Thus, in this manner, clean finish bias binding 16 can comprise one or more fabric strippings 16A that are disposed around entire outer edge 24 of first fabric 20 and entire cuter edge 34 of second fabric 30 to form a closed dual layered surgical wrapper 10 as shown in FIGS. 2A and 2B. By first fabric 20 being a barrier fabric that repel fluids, such as wafer and other liquids, and by having the instruments residing on and adjacent the barrier fabric of first fabric 20 when the instruments are wrapped, surgical wrapper 10 can facilitate the steam sterilization of surgical items that are stored therein and also facilitate the maintenance of the sterility of those surgical items. When second fabric 30 is an absorbent fabric, second fabric 30 can be used to facilitate clean-up of fluids around the operating area during surgery. Dual layered surgical wrapper 10 can then be processed through approved laundering and steam sterilization processes so that dual layered surgical wrapper 10 can be used again, in some embodiments, surgical wrapper 10 can include an RFID tag to aid in tracking usage.

Figure 3:
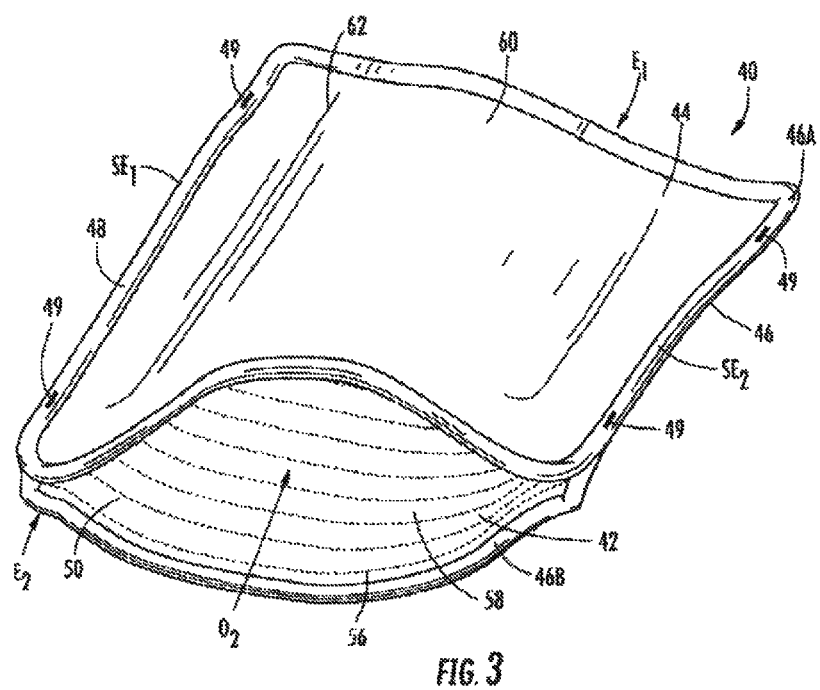
FIG. 3 illustrates a perspective view of another embodiment of a reusable surgical wrapper according to the subject matter disclosed herein.

FIGS. 3 and 4 illustrate a further embodiment of a surgical wrapper, generally designated 40, according to the present disclosure. As above, surgical wrapper 40 can comprise a first layer 42 and a second layer 44. FIG. 3 shows surgical wrapper 40 from an end $E_2$ with second layer 44 on top and above first layer 42. FIG. 4 shows surgical wrapper 40 from an end $E_1$ that is opposite of end $E_2$ with first layer 42 on top and above second layer 44. First layer 42 can comprise a first fabric 50 that can repel fluids and second layer 42 of surgical wrapper 40 can comprise a second fabric 60. As described above, with reference to surgical wrapper 10 in FIGS. 2A and 2B, surgical wrapper 40 shown in FIGS. 3 and 4 can comprise different sizes for different uses. For example, surgical wrapper 40 can comprise sizes such as about 18 inches×about 18 inches, about 24 inches×about 24 inches, about 30 inches×about 30 inches, about 36 inches×about 36 inches, about 45 inches×about 45 inches, about 54 inches×about 54 inches, and about 72 inches×about 72 inches. Further, surgical wrapper 40 can be made to specified dimensions based on the application. In some embodiments, surgical wrapper 40 can include an RFID tag to aid in tracking usage.

First layer 42 and second layer 44 of surgical wrapper 40 can have a seam binding 46 that binds first layer 42 and second layer 44 together only on sides $SE_1$, $SE_2$ on an outer perimeter 46 of surgical wrapper 40 and leaves ends $E_1$, $E_2$ unbound to form dual layered surgical wrapper 40 that has an opening $O_1$ on end $E_1$, and an opening $O_2$ on end $E_2$. In this manner, first layer 42 and second layer 44 of surgical wrapper 40 form openings therebetween to expose an interior face 58 of first fabric 50 and an interior face 68 of second fabric 60. In such embodiments, openings $O_1$, $O_2$ at ends $E_1$, $E_2$ of dual layered surgical wrapper 40 form an aperture through surgical wrapper 40. Openings $O_1$, $O_2$ at ends $E_1$, $E_2$ allow surgical wrapper 40 to be inspected more easily. In particular, openings $O_1$, $O_2$ at ends $E_1$, $E_2$ allow a light wand to be inserted between first layer 42 and second layer 44 to permit first fabric 50 and second fabric 60 to be inspected during processing for holes therein. If holes are found then that surgical wrapper 40 is repaired or discarded. In some embodiments, seam binding 46 can bind first layer 42 and second layer 44 on one of ends $E_1$, $E_2$ so that just the other of the ends $E_1$, $E_2$ is opened.

First and second fabrics 50, 60 can comprise woven or knitted fabrics. In some embodiments, first and second fabrics 50, 60 can comprise synthetic yarns or yarns comprising synthetic fibers or blends of synthetic and natural fibers. Further, in some embodiments, first and second fabrics 50, 60 can comprise solution dyed fibers or yarns as explained above.

First fabric 50 can form a first exterior face 52 of surgical wrapper 40 and second fabric 60 can form a second exterior face 62 of surgical wrapper 40. As with the closed embodiment described above with reference to FIGS. 2A and 2B, barrier fabric 50 of first layer 42 can comprise a woven fabric. For example, first fabric 50 can comprise a polyester fabric that can comprise polyester yarns that can be tightly woven. For example, in some embodiments, first fabric 50 can comprise warp yarns and/or fill yarns that can comprise texturized polyester filament yarns or variations thereof and fill yarns that can comprise texturized polyester filament yarns or variations thereof. As stated above, first fabric 50 can comprise a tightly woven polyester fabric. For example, first fabric 50 can have between about 135 and about 200 ends per inch and between about 70 to about 125 picks per inch. The polyester fabric of first fabric 50 can be finished to make it fluid repellent. Commercially available chemicals can be used in the finishing process to increase repellency. First fabric 50 can vary in weight and size. For example, in some embodiments, first fabric 50 can, for example, have a weight per unit area of about 2 oz/yd$^2$ and about 4 oz/yd$^2$. As above, in some embodiments, first fabric 50 can comprise a plurality of static dissipative yarns 56. For example, the plurality of static dissipative yarns 56 can comprise carbon filament yarns.

Like second fabric 30 of surgical wrapper 10 shown in FIGS. 2A and 2B, second fabric 60 of second layer 42 of surgical wrapper 40 shown in FIGS. 3 and 4 can comprise a fabric, for example, polyester fabric, that can be either a barrier fabric or an absorbent fabric depending on the application, in some embodiments, second fabric 60 can be a barrier fabric that can comprise woven polyester yarns that are treated with a fluid repellent finish in a similar manner to first fabric 50 that can be a barrier fabric. In some embodiments, for example, the polyester fabric of second fabric 50 can comprise woven polyester yarns, such as spun polyester yarns, that are treated to create absorbency. In particular, the polyester fabric of second fabric 60 can be treated and processed to form an absorbent fabric. Additionally, second fabric 60 can comprise a tightly woven polyester fabric having, for example, between about 90 and about 140 ends per inch and between about 65 and about 100 picks per inch. Second fabric 60 can vary in weight and size. For example, in some embodiments, second fabric 60 can, for example, be a spun polyester woven fabric that has a weight per unit area of between about 4 oz/yd$^2$ and about 5 oz/yd$^2$.

To make the naturally hydrophobic polyester fabric into second fabric 60, the fabric and the polyester yarns therein can be treated with chemicals such as in a finishing process to make the polyester fabric absorbent and hydrophilic. For example, the polyester fabric of second fabric 60 can be INFUSED® fabrics sold by Hinson & Hale Medical Technologies, Inc., which can be highly absorbent.

Clean finish bias binding 46 can be made of different material and can be made of a plurality of pieces or strips, in some embodiments, as above, seam binding 46 can be strips of fabric, such as fabric strippings 46A, 46B that can be used to seal off the outer perimeter 48 of dual layered surgical wrapper 40. Clean finish bias binding 46 and fabric strippings 46A, 46B will be explained in more detail with reference to FIGS. 3, 4, 5A, and 5B. In some embodiments of surgical wrappers 40 with openings $O_1$, $O_2$ at ends $E_1$, $E_2$, one or more fabric strippings 46B can be disposed around at least a portion of an cuter edge 54 (see FIG. 5B) of first fabric 50 to seal the portion of outer edge 54 that would otherwise be exposed, for example, around the portions of outer edge 54 of first fabric 50 at ends $E_1$, $E_2$. Similarly, one or more fabric strippings 46A can be disposed around at least a portion of an outer edge 64 (see FIG. 5B) of second fabric 60 to seal outer edge 64. Further, one or more fabric strippings 46A can be used to extend around both outer edge 54 of first fabric 50 and outer edge 64 of second fabric 60 on sides $SE_1$ and $SE_2$ of surgical wrapper 40 to bind first fabric 50 of first layer 42 and second fabric 60 of second layer 44 together.

Fabric strippings 46A, 46B can be tightly woven polyester fabric. Fabric strippings 46A, 46B can be of different widths and lengths. The width of each fabric strippings 46A, 46B can depend on the amount of overlap of fabric stripping 46A on exterior face 52 of first fabric 50 and exterior face 62 of second fabric 60 (see FIGS. 3 and 4). For example, fabric strippings 46A, 46B can be about 1.5 inches in width and can be folded to a clean finish of about 0.5 inch on exterior faces 52, 62 of first fabric 50 and second fabric 60, respectively. The length can depend on the size of surgical wrapper 40 and the length of its outer perimeter 48 (see FIGS. 3 and 4) and/or outer edges 54, 64 of first fabric 50 and second fabric 60, respectively. The length can also depend on the number of fabric strippings 46A, 46B that are used in surgical wrapper 40.

Figure 5A:
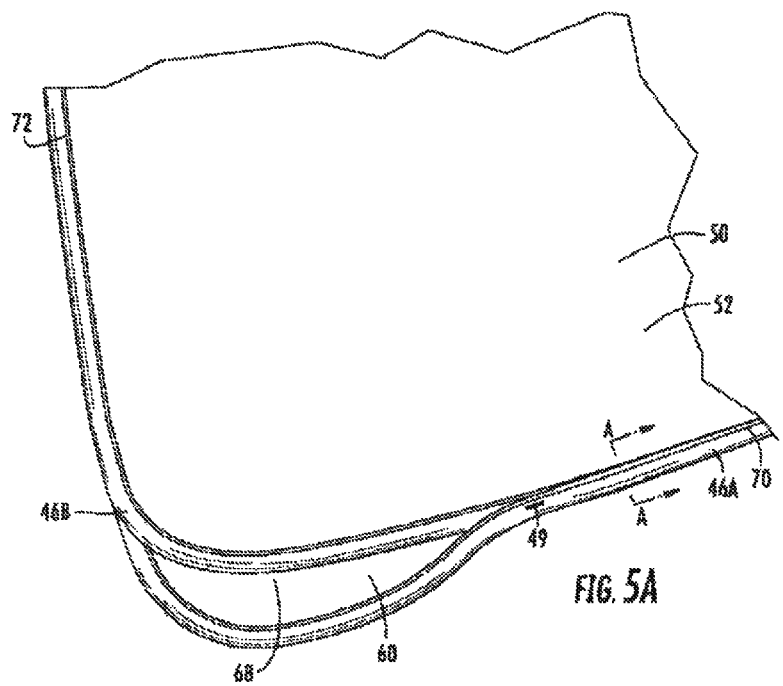
FIG. 5A illustrates a perspective view of a portion of another embodiment of a reusable surgical wrapper according to the subject matter disclosed herein.
Figure 5B:
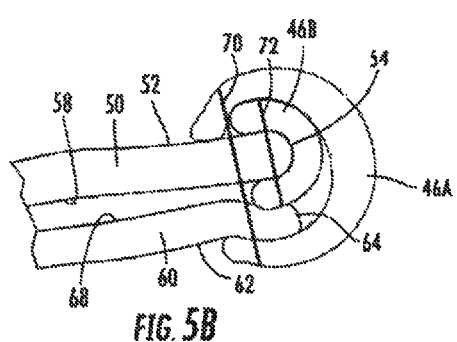
FIG. 5B illustrates a cross-sectional schematic view of a portion of the embodiment of the surgical wrapper according to FIG. 5A taken along the lines A-A.

As above, fabric strippings 46A, 46B of seam binding 46 can be secured around cuter edge 54 of first fabric 50 and outer edge 64 of second fabric 60 in different manners. In the embodiment shown in FIGS. 3, 4, 5A, and 5B, fabric strippings 46A, 46B of seam binding 46 can be secured around outer edge 54 of first fabric 50 and outer edge 64 of second fabric 60 by stitching 70 and 72. The stitching can be a spun polyester thread. Stitching 72 can be used to secure fabric stripping 46B around outer edge 54 of first fabric 50 as shown in FIGS. 5A and 5B. Similarly, stitching 70 can be used to secure fabric stripping 46A around outer edge 54 of first fabric 50. Further, at sides $SE_1$, $SE_2$ of surgical wrapper 40 where fabric stripping 46A overlaps both outer edge 54 of first fabric 50 and outer edge 64 of second fabric 60 and also fabric stripping 46B, stitching 70 can also be used to secure fabric stripping 46A, outer edge 54 of first fabric 50, and outer edge 64 of second fabric 60 together as shown in FIG. 5B. Further, to strengthen seam binding 46 at the portion of surgical wrapper 40 where first fabric 50 and second fabric 60 are first joined at the junctures of the two fabrics 50, 60, bar tack stitching 49 can be provided that is more dense that normal stitching. Bar tack stitching 49 can help to prevent tearing and ripping at these junctures. In this manner, surgical wrapper 40 can be bound on sides $SE_1$, $SE_2$ while providing openings $O_1$, $O_2$ at ends $E_1$, $E_2$ of surgical wrapper 40.

Figure 6A:
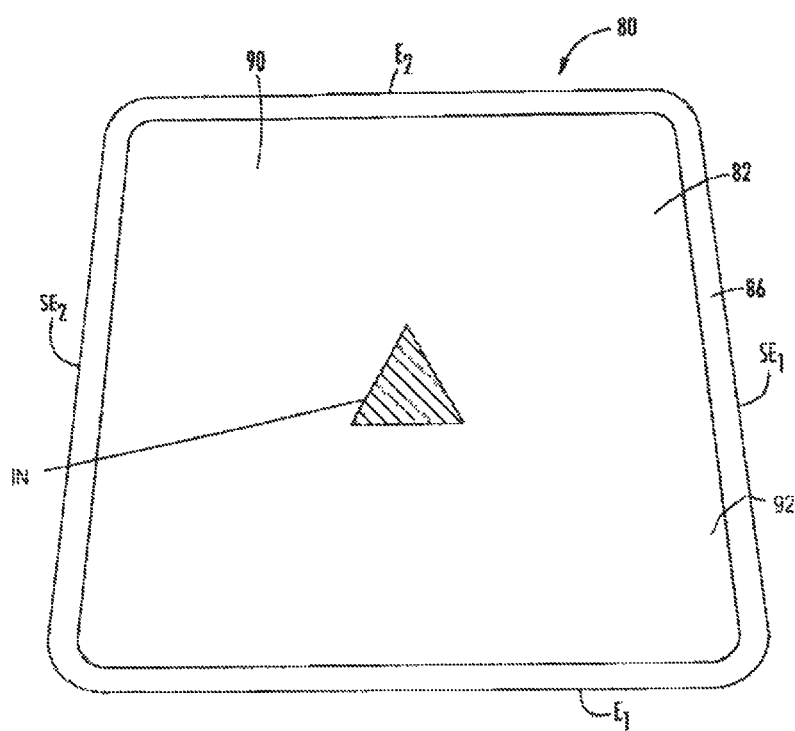
FIGS. 6A-6B illustrate perspective views of another embodiment of a reusable surgical wrapper according to the subject matter disclosed herein.
Figure 6B:
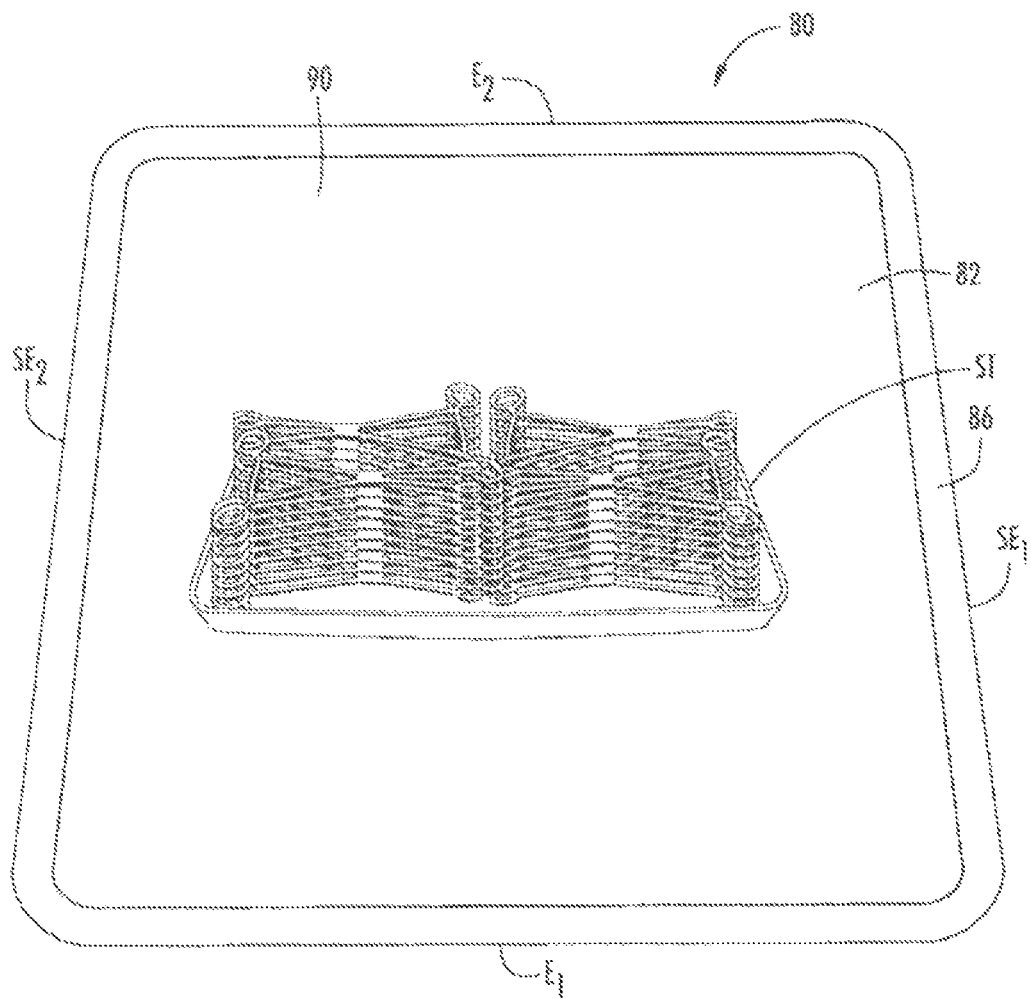

FIGS. 6A-6B illustrate the use of an embodiment of a closed dual layered surgical wrapper 80 to wrap a basket of surgical instruments SI to be steam sterilized and preserved for use. As shown in FIG. 6A surgical wrapper 80 can be laid flat with a first layer 82 of a first barrier fabric 90 facing upward. First layer 82 of first barrier fabric 90 can be bound to a second layer 84 of a second barrier fabric (not shown) by a seam binding 86. An indicator IN as represented by the triangle on first barrier fabric 90 can be used to indicate the correct orientation of wrapper 80 and the center of surgical wrapper 80, for example, relative to a label or RFID tag or chip. In particular, indicator IN can be disposed on the exterior face 92 of fabric 90. Indicator IN can be shaped to indicate the direction to orientate wrapper 80 for folding and how the surgical instruments SI are to be placed on surgical wrapper 80. For example, indicator IN can be an arrow pointing up or a logo that is positioned a specific way. Indicator IN can be a decal, or can be printed on the fabric. In some embodiments, indicator IN can be woven or embroidered into fabric 90. Indicator IN can be shaped to indicate how and where the surgical instruments SI are placed on wrapper 80 relative to the corners of wrapper 80 and the label or RFID tag or chip, so that, once wrapper 80 is folded, the label or RIFD tag or chip can be located on the folded wrapper 80 at the same conspicuous and easy readable place to increase the efficiency of the operating room staff.

As shown in FIG. 6B, the surgical wrapper 80 is oriented with the pointed portion of the IN pointing away from the sterile supply employee (as shown in FIG. 6A) and the basket of surgical instruments SI can be placed on indicator IN at the center of surgical wrapper 80. Instead of indicating that long sides of the basket of surgical instruments SI should be placed parallel with the ends $E_1$, $E_2$ of the wrapper 80 as shown in FIG. 6B, the indicator IN can notify hospital staff to place the basket of surgical instruments SI at a different angle relative to the ends $E_1$, $E_2$ and the corners of wrapper 80. Far example, the basket of surgical instruments SI can be placed on wrapper 80 so that wrapper 80 forms a diamond shape around the basket of surgical instruments SI relative the long sides of the basket, instead of a square shape. Once the surgical instruments SI are properly placed, surgical wrapper 80 can then be folded according to industry folding standards, such as ANSI/AAMI ST79: 2006 and ANSI/AAMI ST 79/A1:2008. For example, indicator IN can be oriented to indicate how and where surgical instruments SI are to be placed relative to the corners of wrapper 80 and relative to where the label or RIFD tag or chip that is located on wrapper 80 will end up once the surgical wrapper 80 is properly folded to enclose the instruments or container(s) of instruments therein.

As stated above, the surgical wrappers disclosed herein are devices intended to be used to enclose another medical device that is to be sterilized by a health care provider. The surgical wrappers of the subject matter disclosed herein can allow sterilization of medical devices and instruments wrapped and enclosed therein and can also maintain sterility of the enclosed device until use. The surgical wrappers can be provided non-sterile and can be processed before use. The surgical wrappers disclosed herein can be subject to approved laundering and sterilisation processes and can be reused a number of times. For example, the surgical wrappers disclosed herein can be reprocessed based on industrial laundering and steam sterilization procedures that include a prevacuum setting at a 270° F. temperature for 4 minutes with 20 minutes drying time.

The number of reprocessing cycles (laundering and steam sterilization) dual layered surgical wrappers disclosed herein can go through can vary. For example, the number of reprocessing cycles can be between about 2 and about 150 processing cycles for the dual layered surgical wrappers depending on the user and the application. For instance, the number of reprocessing cycles can be between about 50 and about 150 processing cycles. The number of reprocessing cycles can depend upon the environment in which the dual layered surgical wrapper is used and the use of industry practices for laundering and sterilization for similar medical devices, for example.

Embodiments of the present disclosure shown in the drawings and described above are exemplary of numerous embodiments that can be made within the scope of this disclosure. It is contemplated that the devices and related methods can comprise numerous configurations other than those specifically disclosed.

What is claimed is:

1. A reusable dual layered surgical wrapper comprising:
   a first layer comprising a first fabric that is a barrier fabric that repels fluids forming a first exterior face of the surgical wrapper, such that the first layer repels fluids;
   a second layer comprising a second fabric forming a second exterior face of the surgical wrapper, the second fabric comprising woven polyester yarns that are treated to form an absorbent fabric, such that the second layer is absorbent; and
   the first fabric having an outer edge and the second fabric having an outer edge, the first fabric and the second fabric being bound together along at least a portion of both the outer edge of the first fabric and the outer edge of the second fabric to join the first layer and the second layer, such that the first layer and the second layer form openings at two opposing ends of the dual layered surgical wrapper with the openings forming an aperture through the dual layered surgical wrapper to expose an interior face of the first fabric and an interior face of the second fabric so that the dual layered surgical wrapper is configured to allow a light wand to be inserted between the first layer and the second layer to permit the first fabric and the second fabric to be inspected during processing for holes therein; and
   the first fabric forming the first exterior face and the first interior face of the surgical wrapper on a first side of the opening and the second fabric forming the second exterior face and the second interior face of the surgical wrapper on a second side of the opening such that the first layer that forms the first side of the opening repels fluids and the second layer that forms the second side of the opening is absorbent.

2. A surgical wrapper comprising:
   a first layer comprising a first fabric that is a barrier fabric that repels fluids forming a first exterior face of the surgical wrapper, such that the first layer repels fluids;
   a second layer comprising a second fabric forming a second exterior face of the surgical wrapper, the second fabric comprising woven polyester yarns that are treated to form an absorbent fabric, such that the second layer is absorbent; and
   a clean finish bias binding disposed around at least a portion of an outer edge of the first fabric and an outer edge of the second fabric to join the first layer and the second layer to form a dual layered surgical wrapper such that the first layer and the second layer form openings at two opposing ends of the dual layered surgical wrapper with the openings forming an aperture through the dual layered surgical wrapper to expose an interior face of the first fabric and an interior face of the second fabric so that the dual layered surgical wrapper is configured to allow a light wand to be inserted between the first layer and the second layer to permit the first fabric and the second fabric to be inspected during processing for holes therein; and
   the first fabric forming the first exterior face and the first interior face of the surgical wrapper on a first side of the opening and the second fabric forming the second exterior face and the second interior face of the surgical wrapper on a second side of the opening such that the first layer that forms the first side of the opening repels fluids and the second layer that forms the second side of the opening is absorbent.

3. The surgical wrapper according to claim 2, wherein the first fabric comprises woven polyester yarns.

4. The surgical wrapper according to claim 2, wherein the first fabric comprises a plurality of static dissipative yarns.

5. The surgical wrapper according to claim 2, wherein the clean finish bias binding comprises one or more fabric strippings that are disposed around at least a portion of the outer edge of the first fabric and one or more fabric strippings that are disposed around at least a portion of the outer edge of the second fabric with the one or more fabric strippings disposed around at least a portion of the outer edge of the first fabric and one or more fabric strippings disposed around at least a portion of the outer edge of the second fabric at least partially overlapping on opposing sides of the dual layered surgical wrapper.

6. The surgical wrapper according to claim 2, further comprising an indicator on the first face of the dual layered surgical wrapper positioned at a center of the first layer to provide guidance for orientation of the wrapper and placement of surgical instruments on the dual layered surgical wrapper.

7. The surgical wrapper according to claim 1, wherein the first fabric and the second fabric comprise at least one of synthetic fibers or synthetic yarns, the synthetic fibers or synthetic yarns comprise synthetic material that has color pigment added to the synthetic material before extrusion into fibers or yarns.

8. The surgical wrapper according to claim 2, wherein the first fabric and the second fabric comprise at least one of synthetic fibers or synthetic yarns, the synthetic fibers or synthetic yarns comprise synthetic material that has color pigment added to the synthetic material before extrusion into fibers or yarns.

* * * * *